United States Patent
Ohishi (10) Patent No.: US 8,929,633 B2
(45) Date of Patent: Jan. 6, 2015

(54) DIAGNOSTIC X-RAY SYSTEM AND METHOD

(75) Inventor: Satoru Ohishi, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 1062 days.

(21) Appl. No.: 12/752,518

(22) Filed: Apr. 1, 2010

(65) Prior Publication Data

US 2010/0278410 A1 Nov. 4, 2010

(30) Foreign Application Priority Data

Apr. 10, 2009 (JP) ................................ 2009-096181
Mar. 29, 2010 (JP) ................................ 2010-075984

(51) Int. Cl.
*G06K 9/00* (2006.01)
*A61B 6/00* (2006.01)
*A61B 6/03* (2006.01)

(52) U.S. Cl.
CPC ............... *A61B 6/504* (2013.01); *A61B 6/5235* (2013.01); *A61B 6/032* (2013.01); *A61B 6/466* (2013.01); *A61B 6/541* (2013.01); *A61B 6/4441* (2013.01); *A61B 6/503* (2013.01); *A61B 6/481* (2013.01)
USPC ........................................................ 382/131

(58) Field of Classification Search
USPC ........................................................ 382/131
See application file for complete search history.

(56) References Cited

U.S. PATENT DOCUMENTS

| | | | |
|---|---|---|---|
| 7,496,175 B2 | 2/2009 | Sakaguchi et al. | |
| 7,505,549 B2 * | 3/2009 | Ohishi et al. | 378/4 |
| 7,805,181 B2 * | 9/2010 | Breeuwer | 600/419 |
| 8,094,912 B2 * | 1/2012 | Miyamoto et al. | 382/131 |
| 8,160,338 B2 * | 4/2012 | Ichihara et al. | 382/131 |
| 8,265,224 B2 * | 9/2012 | Baumgart | 378/95 |
| 2004/0057607 A1 * | 3/2004 | Breeuwer et al. | 382/128 |

(Continued)

FOREIGN PATENT DOCUMENTS

| | | |
|---|---|---|
| JP | 2002-199279 | 1/2002 |
| JP | 2007-136164 | 6/2007 |
| JP | 2008-136800 | 6/2008 |
| JP | 2008-220464 | 9/2008 |

OTHER PUBLICATIONS

U.S. Appl. No. 12/708,667, filed Feb. 19, 2010.

(Continued)

*Primary Examiner* — Robert Sorey
(74) *Attorney, Agent, or Firm* — Oblon, Spivak, McClelland, Maier & Neustadt, L.L.P.

(57) ABSTRACT

A diagnostic x-ray system includes a CT-image projection unit obtains a third perfusive-flow image by projecting a second perfusive-flow image obtained by computed tomography in the same direction as a projection direction in which an X-ray is projected toward a test subject to obtain a first perfusive-flow image. A positioning unit obtains positioning information by performing positioning of the first perfusive-flow image and the third perfusive-flow image. A perfusive-flow index calculation unit calculates a first perfusive-flow index from the first perfusive-flow image, and calculates a second perfusive-flow index from the third perfusive-flow image. A comparative-index calculation unit calculates a comparative index based on the first perfusive-flow index and the second perfusive-flow index, by comparing the first perfusive-flow index with the second perfusive-flow index, based on the positioning information obtained by the positioning unit.

9 Claims, 7 Drawing Sheets

(56) References Cited

U.S. PATENT DOCUMENTS

| | | | |
|---|---|---|---|
| 2005/0002549 A1* | 1/2005 | Nay et al. | 382/130 |
| 2006/0155185 A1* | 7/2006 | Breeuwer | 600/407 |
| 2007/0092067 A1* | 4/2007 | Fujisawa | 378/196 |
| 2008/0044073 A1* | 2/2008 | Bernhardt et al. | 382/128 |
| 2008/0107233 A1* | 5/2008 | Sakaguchi et al. | 378/91 |
| 2008/0273782 A1* | 11/2008 | Ichihara | 382/131 |
| 2009/0028409 A1* | 1/2009 | Tsukagoshi et al. | 382/131 |
| 2009/0281415 A1* | 11/2009 | Cupps et al. | 600/410 |
| 2009/0297008 A1* | 12/2009 | Taxt et al. | 382/131 |
| 2010/0278405 A1* | 11/2010 | Kakadiaris et al. | 382/131 |

OTHER PUBLICATIONS

U.S. Appl. No. 12/700,195, filed Feb. 4, 2010, Ko Fuchigami et al.
Japanese Office Action mailed Oct. 15, 2013 in Japanese Patent Application No. 2010-075984.

* cited by examiner

DIAGNOSTIC X-RAY SYSTEM AND METHOD

CROSS-REFERENCE TO RELATED APPLICATIONS

This application is based upon and claims the benefit of priority from prior Japanese Patent Applications No. 2009-096181, filed Apr. 10, 2009; and No. 2010-075984, filed Mar. 29, 2010, the entire contents of both of which are incorporated herein by reference.

BACKGROUND OF THE INVENTION

1. Field of the Invention

The present invention relates to a diagnostic x-ray system and a method thereof used to practice perfusion using CT images of, for example, coronary arteries and brain portions of a test subject which are obtained by computed tomography, and X-ray images obtained by the diagnostic x-ray system, in order to diagnose and care the test subject.

2. Description of the Related Art

Perfusion using a CT device and a diagnostic x-ray system are very significant to diagnose a test subject such as a human body and to identify therapy effects. For perfusion, there are a method for performing an analysis by using a CT image obtained by a CT device, and a method for performing an analysis by using an X-ray image obtained by a diagnostic x-ray system are overlapped each other.

Meanwhile, for a medical operation for myocardial ischemia, there is a manipulation in which a catheter is inserted up to a narrowed portion and a balloon attached to the catheter is spread to enhance the narrowed portion. For a medical operation for a cerebral aneurysm, there is a manipulation in which a catheter is inserted up to a cerebral aneurysm and a coil is projected from a tip end of the catheter, to stuff the cerebral aneurysm with the coil. Medical operations using a catheter are called interventions, and recently attract much interest as a medical care which requires less invasion than an surgical cure.

To check perfusion in a test object, use of CT images obtained by a CT device or MRI images obtained by a MRI device before a medical operation of the intervention is most preferred as a modality. In the intervention, there is no other way but using X-ray images obtained by a diagnostic x-ray system when checking a therapeutic process or when finally checking a medical care.

A technique relevant to perfusion of a test subject is disclosed in, for example, Jpn. Pat. Appln. KOKAI Publication No. 2008-136800. This publication discloses that an index representing an inflow state of blood and an index representing an outflow state of blood are calculated about a local coronary muscle such as a myocardium of a test subject.

To know improvements in inflow and outflow states of blood into and from a coronary artery of a test subject between before and after a medical care, indices representing inflow and outflow states of blood need be compared. To compare the indices, perfusion need be practiced with use of a diagnostic x-ray system both before and after a medical care. To practice perfusion, which has already analyzed by a CZT device, again with use of a diagnostic x-ray system is to expose the test subject to X-rays for a clinically less worthy purpose.

The invention has an object of providing a diagnostic x-ray system and a method thereof capable of comparing perfusion before and after a medical cure without increasing an exposure dose.

BRIEF SUMMARY OF THE INVENTION

A diagnostic x-ray system according to a first aspect of the present invention comprises a CT-image projection unit that obtains a third perfusive-flow image by projecting a second perfusive-flow image obtained by computed tomography in the same direction as a projection direction in which an X-ray is projected toward a test subject to obtain a first perfusive-flow image, a positioning unit that obtains positioning information by performing positioning of the first perfusive-flow image and the third perfusive-flow image, a perfusive-flow index calculation unit that calculates a first perfusive-flow index from the first perfusive-flow image, and calculates a second perfusive-flow index from the third perfusive-flow image, and a comparative-index calculation unit that calculates a comparative index based on the first perfusive-flow index and the second perfusive-flow index, by comparing the first perfusive-flow index with the second perfusive-flow index, based on the positioning information obtained by the positioning unit.

A diagnostic X-ray method according to a second aspect of the present invention comprises obtaining a third perfusive-flow image by projecting a second perfusive-flow image obtained by computed tomography in the same direction as a projection direction in which an X-ray is projected toward a test subject to obtain a first perfusive-flow image, obtaining positioning information by performing positioning of the first perfusive-flow image and the third perfusive-flow image, calculating a first perfusive-flow index from the first perfusive-flow image, and calculates a second perfusive-flow index from the third perfusive-flow image, and calculating a comparative index based on the first perfusive-flow index and the second perfusive-flow index, by comparing the first perfusive-flow index with the second perfusive-flow index, based on the positioning information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of the invention will be described with reference to the drawings.

Terms will be described first. "Perfusive flow" means blood flow to myocardia.

A "perfusive flow image" is an image which photographs blood flow to myocardia.

"Myocardial perfusion" and "myocardial perfusive flow" both clinically have the same meaning as a phrase expressing a phenomenon that blood flows into and out of capillaries. In this description, however, perfusive flow images and perfusion images are distinguished as follows. A perfusive flow image is defined to be an image obtained by picking up a state in which blood reaches myocardia from capillaries. A perfusion image is defined to be an image obtained by analyzing and converting the perfusive flow image into perfusion indices.

X-ray perfusion-flow images are perfusive flow images representing intensity distribution of an X-ray which has penetrated a test subject Q.

Figure 1:
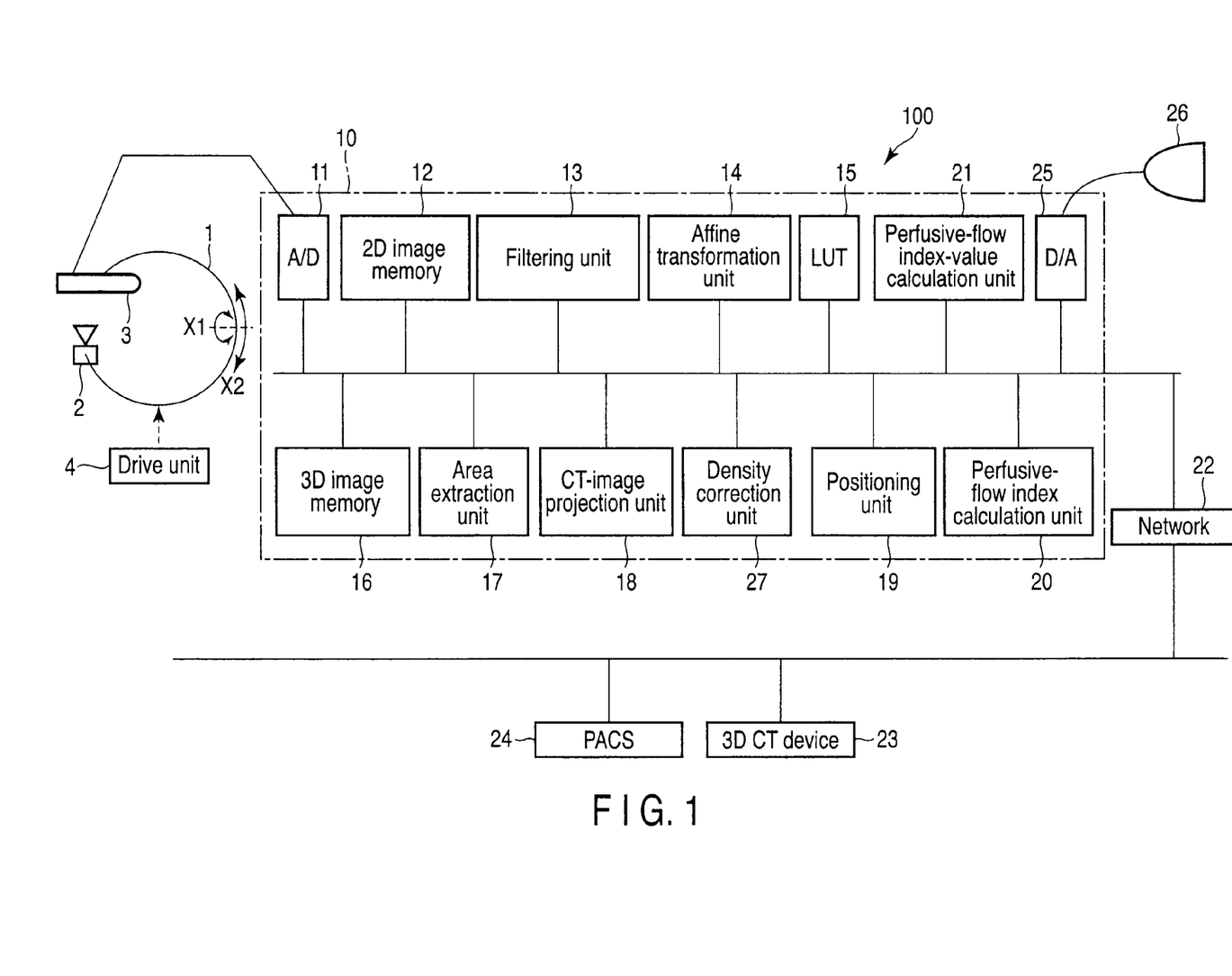
FIG. 1 is a block diagram illustrating an embodiment of a diagnostic x-ray system according to the invention.
Figure 2:
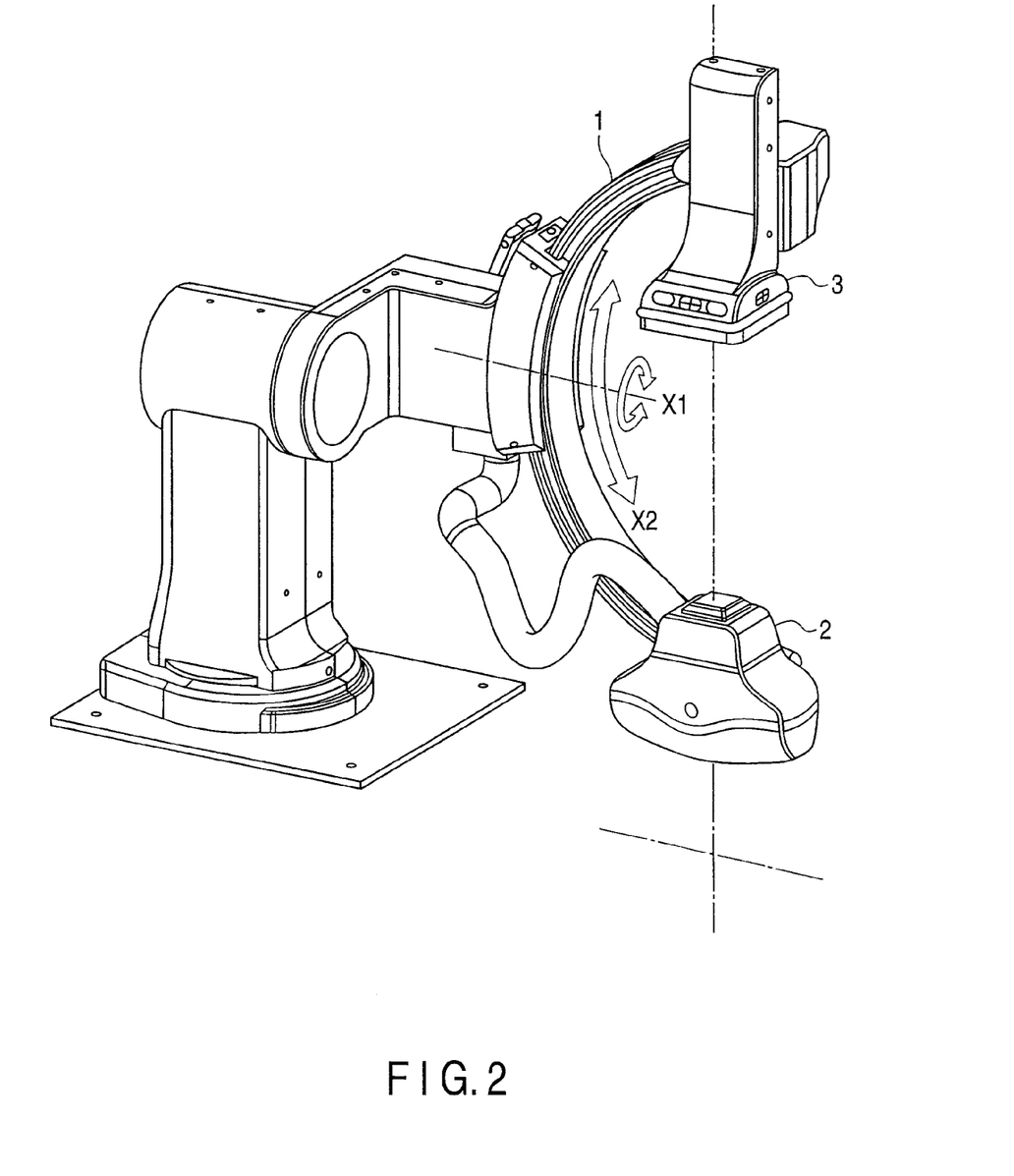
FIG. 2 is a perspective view illustrating a mechanism of a C-shaped arm in the diagnostic x-ray system.

FIG. 1 is a block diagram drawing a configuration of a diagnostic x-ray system 100 (hereinafter referred to as the present system). FIG. 2 is a perspective view of a C-shaped arm 1. The system 100 performs common X-ray angiographic imaging (an angiographic examination method). An X-ray bulb tube 2 is provided at an end of the arm 1, and an X-ray detector 3 is provided at another end thereof. The X-ray detector 3 uses an X-ray image intensifier (I.I.) or a flat panel detector (FPD). A table is provided between the X-ray bulb tube 2 and an X-ray detector 3. A patient as a test subject is set on the table. The arm 1 rotates about a first axis X1 and a second axis X2. When the arm 1 rotates about the first axis X1, the test subject is imaged in right and left oblique directions relative to the test subject in accordance with movement of the X-ray bulb tub 2 and X-ray detector 3 as the arm 1 rotates. When the arm 1 rotates about the second axis X2, the test subject is imaged in upper and lower oblique directions relative to the test subject in accordance with movement of the X-ray bulb tube 2 and X-ray detector 3 as the arm 1 rotates. In actual, the arm rotates about the first axis X1 and second axis X2 combined with each other, and imaging is performed in an upper left oblique direction or in a lower right oblique direction relative to the test subject, for example.

An image processing device 10 projects a perfusive flow image (CT perfusive-flow image) obtained by computed tomography (hereinafter referred to as CT), in the same direction as a projection direction in which the X-ray image (X-ray perfusive-flow image) is obtained by the diagnostic x-ray system (hereinafter referred to as a present system).

The image processing device 10 performs positioning of the X-ray perfusive-flow image and the CT perfusive-flow image, and calculates perfusive flow indices respectively from the X-ray perfusive-flow image and the CT perfusive-flow image. Based on positioning information obtained by positioning the X-ray perfusive-flow image and the CT perfusive-flow image, the image processing device 10 compares the perfusive flow indices of the X-ray perfusive-flow image and the CT perfusive-flow image with each other, and calculates a comparative index between the X-ray perfusive-flow image and the CT perfusive-flow image.

The image processing device 10 collects X-ray perfusive-flow images after a thrombolytic therapy or an intervention for the test subject.

When collecting X-ray perfusive-flow images, the image processing device 10 sets a tube voltage applied to the X-ray bulb tube 2 at the same tube voltage and/or uses the same radiation quality as when collecting perfusive flow images obtained by a three-dimensional (3D) CT device 23.

If a target area is a cardiac area when collecting the X-ray perfusive-flow images, collection of electrocardiographic images having the same cardiac phase as a cardiac phase collected by the three-dimensional (3D) CT device 23 is set.

The image processing device 10 includes an analog/digital (A/D) converter 11, a two-dimensional (2D) image memory 12, a filtering unit 13, an affine transformation unit 14, a lookup table (LUT) 15, a three-dimensional image memory 16, an area extraction unit 17, a CT-image projection unit 18, a positioning unit 19, a perfusive-flow index-value calculation unit 20, a comparative-index calculation unit 21, and a density correction unit 27.

The image processing device 10 is connected to the three-dimensional (3D) CT device 23 and a medical image maintenance communication system (PACS) device 24 through a network 22. The image processing device 10 includes a digital/analog (D/A) converter 25. The D/A converter 25 is connected with a display device 26.

The 3D CT device 23 sequentially collects plural three-dimensional (3D) CT images of coronary arteries of a test subject as time elapses while injecting a contrast medium into the test subject, and 3D CT images are thereby obtained as a motion picture to become perfusive flow images. The perfusive flow images obtained by the 3D CT device 23 are 3D CT images each for calculating a perfusive flow index. Unlike a perfusive flow index which is commonly used for CT, the perfusive flow index described above is calculated in the same method as a method in which an X-ray perfusive flow index is calculated. The 3D CT device 23 collects the CT perfusive-flow images before the thrombolytic therapy or the intervention for the test subject.

The PACS device 24 stores, as digital images, CT images and X-ray images which are obtained by various image diagnosis devices, such as the 3D CT device 23 and the present device 100. The PACS device 24 communicates the digital images between the 3D CT device 23 and the present system 100. The PACS device 24 displays the digital images. The PACS device 24 displays the digital images for the purpose of X-ray interpretation.

The PACS device 24 is connected to the present system 100 through the network 22. The PACS device 24 sends 3D CT images as CT perfusive-flow images obtained by the 3D CT device 23, to the present system 100 through the network 22.

The A/D converter 11 performs digital conversion on an output signal of the X-ray detector 3.

The 2D image memory 7 stores, as X-ray image data, an output signal of the X-ray detector 3 which has been subjected to digital conversion by the A/D converter 11. The X-ray image data consists of X-ray perfusive-flow images which are sequentially obtained by imaging while injecting a contrast medium into a blood vessel.

The filtering unit 13 performs high-frequency emphasis filtering.

The affine transformation unit 14 magnifies and/or moves images.

The LUT 15 is to perform tone conversion.

The 3D image memory 16 stores CT perfusive-flow images sent from the 3D CT device 23 or PACS device 24 through the network 22.

The area extraction unit 17 extracts an image of an interested area from the 3D CT image. Specifically, the area extraction unit 17 receives a CT perfusive-flow image from the 3D CT device 23 or PACS device 24 through the network 22, manually identifies an area which coincides with an X-ray perfusive-flow image from the CT perfusive-flow image, and extracts the area from the CT perfusive-flow image.

Figure 3A:
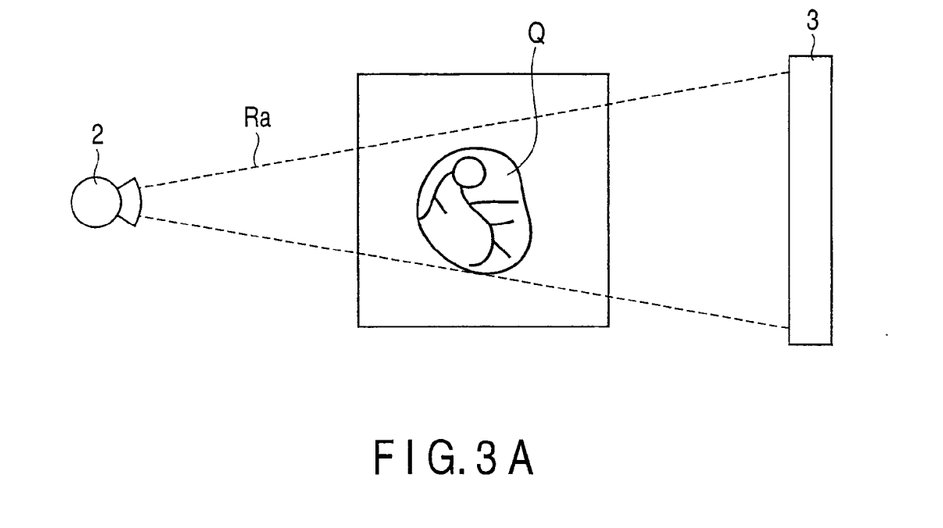
FIG. 3A illustrates a projection direction of obtaining an X-ray perfusive-flow image in the diagnostic x-ray system.
Figure 3B:
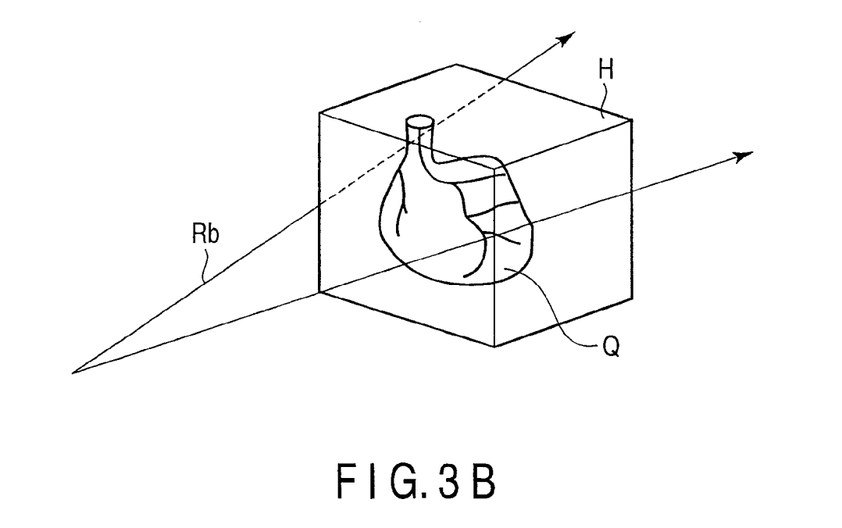
FIG. 3B illustrates a projection direction of obtaining a CT perfusive image obtained by a 3D CT device.

Under the same conditions as those for an X-ray projection geometry when obtaining an X-ray perfusive-flow image, the CT-image projection unit 18 projects a 3D or CT perfusive-flow image obtained by the 3D CT device 23, in the same direction as a projection direction in which an X-ray perfusive-flow image is obtained by the present system 100. FIG. 3A represents the projection direction Ra in which an X-ray perfusive-flow image is obtained. The X-ray bulb tube 2 radiates an X-ray onto a test subject Q. The X-ray detector 3 detects the X-ray which has transmitted through the test subject Q. FIG. 3B represents a projection direction in which a 2D CT image is projected onto a perfusive flow image H. The projection direction Rb to the perfusive flow image H is set in the same direction as the projection direction Ra of the X-ray.

Figure 4:
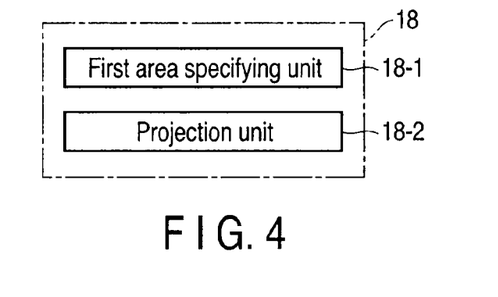
FIG. 4 is a block diagram of a CT-image projection unit in the diagnostic x-ray system.

As illustrated in FIG. 4, the CT-image projection unit 18 includes a first area-specifying unit 18-1 and a projection unit 18-2. The first area-specifying unit 18-1 specifies an area which coincides with an X-ray perfusive-flow image, on a CT perfusive-flow image obtained by the 3D CT device 23. In the 3D CT perfusive-flow image, a contrast medium is injected intravenously, and right and left coronary arteries are simultaneously subjected to contrast-imaging. In the X-ray perfusive-flow image, a contrast medium is also injected intravenously, and only one of right and left coronary arteries is subjected to contrast-imaging. Therefore, where there is an interest in the right coronary artery, analysis need be performed by using a perfusive-flow image including only an area occupied by the right coronary artery among CT perfusive-flow images. The first area-specifying unit 18-1 specifies areas occupied by the respective coronary arteries.

The projection unit 18-2 projects only the area specified by the first area specifying unit 18-1, in the same direction as the projection direction in which the X-ray perfusive-flow image is obtained.

The positioning unit 19 performs positioning of the X-ray perfusive-flow image obtained by the present system 100 and the CT perfusive-flow image. Based on an image including, for example, artery information in the CT perfusive-flow image, the positioning unit 19 performs position alignment between the X-ray perfusive-flow image including the same artery information as the foregoing artery information and the CT perfusive-flow image. The positioning unit 19 performs positioning, for example, based on a shape of a coronary artery in a heart or an outer shape of the heart as a test subject.

The perfusive-flow index-value calculation unit 20 calculates perfusive flow indices respectively from the X-ray and CT perfusive-flow images. Based on the CT perfusive-flow image projected by the CT-image projection unit 18, the perfusive-flow index-value calculation unit 20 calculates a perfusive flow index of the CT perfusive-flow image in the same method as in the method in which the X-ray perfusive-flow index has been calculated.

Figure 5:
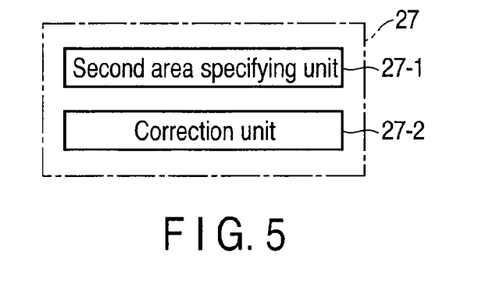
FIG. 5 is a block diagram of a comparative-index projection unit in the diagnostic x-ray system.
Figure 6:
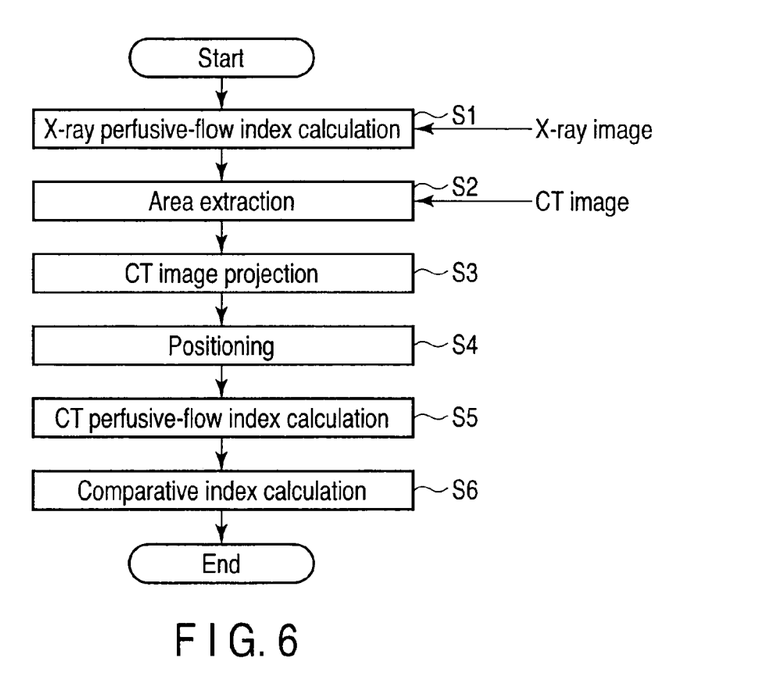
FIG. 6 is a diagnosis flowchart for the diagnostic x-ray system.
Figure 7:
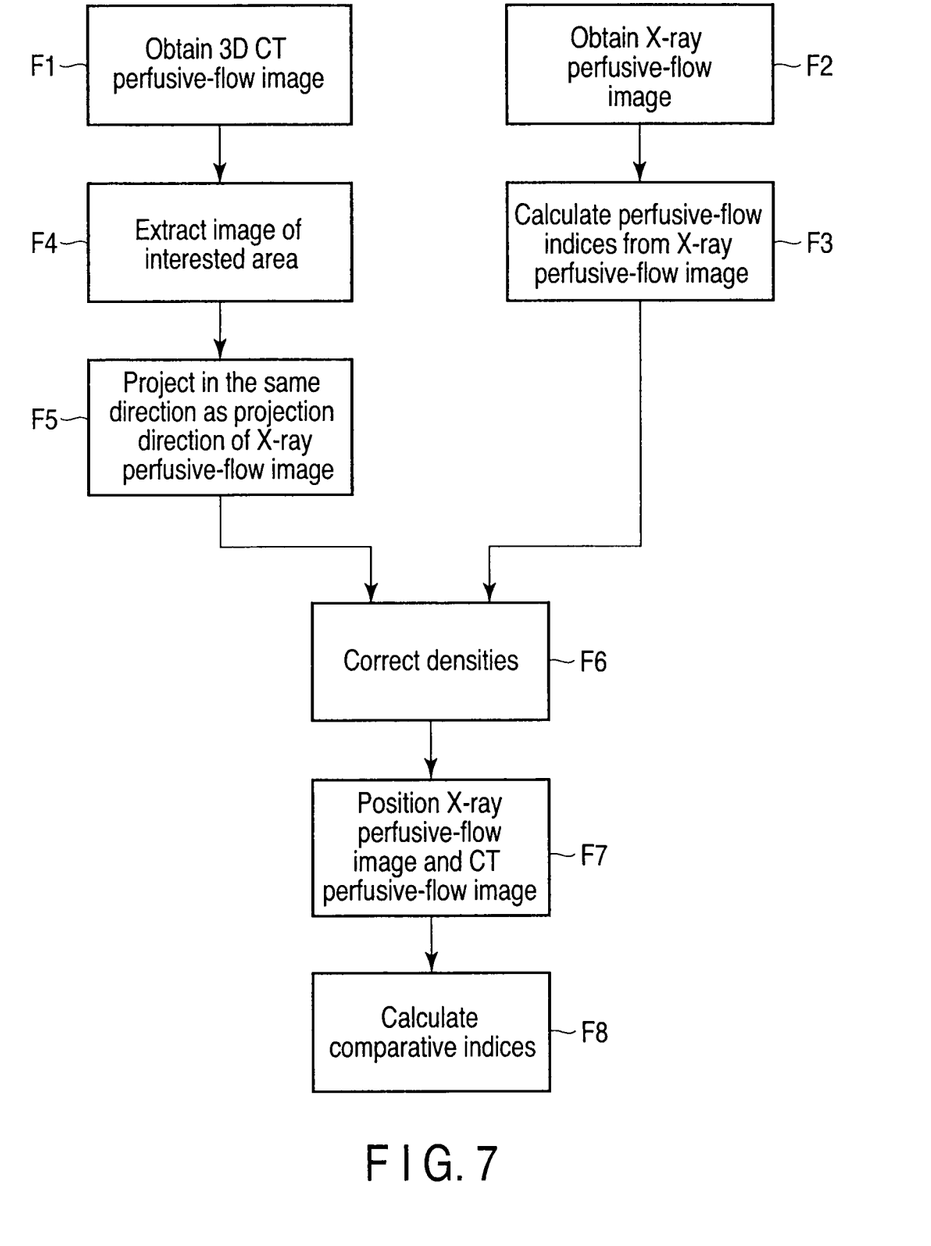
FIG. 7 illustrates flow of perfusion using the diagnostic x-ray system and a CT device.

The density correction unit 27 includes a second area-specifying unit 27-1 and a correction unit 27-2, as illustrated in FIG. 5. The second area-specifying unit 27-1 specifies areas in which perfusive flows are considered to not change between and after a medical care, from the perfusive-flow image of the 3D CT device 23 and the X-ray perfusive-flow image obtained by the present system 100. The correction unit 27-2 makes a correction in a manner that Further, based on positioning information obtained by the positioning unit 19, the comparative-index calculation unit 21 compares the perfusive flow index calculated from the X-ray perfusive-flow index with the perfusive flow index calculated from the CT perfusive-flow image, thereby to calculate a comparative index between the X-ray and CT perfusive-flow images. The comparative index is a ratio or difference, for example, between the X-ray perfusive-flow index and the CT perfusive-flow index. The comparative index calculated by the comparative-index calculation unit 21 is displayed, regularly arranged together with the X-ray perfusive-flow index, on the display device 26, Next, operation of the system configured as described above will now be described along a diagnosis flowchart drawn in FIG. 6. FIG. 7 represents a flow of perfusion using the CT device and diagnostic x-ray system.

Perfusion of the test subject is checked by using a CT image obtained by the 3D CT device 23. The 3D CT device 23 sequentially collects 3D CT perfusive-flow images while injecting a contrast medium into the test subject along the first flow F1. The 3D CT perfusive-flow images are collected to calculate perfusion in coronary arteries of the test subject Q. When cardiac capillaries or myocardia are evaluated, perfusive images are collected by imaging only middiastolic or telesystolic data for which motion is the smallest in a cardiac cycle in synchronization with electrocardiograms. When there is no motion, e.g., for a head, perfusive-flow images are collected by sequential imaging regardless of electrocardiograms. The 3D CT device 23 collects the 3D CT perfusive-flow images, and thereby obtains the 3D CT perfusive-flow images for plural cycles.

The 3D CT perfusive-flow images for plural cycles obtained by the 3D CT device 23 are stored as digital images in the PACS device 24. Normally, perfusive-flow index values such as an inflow speed, an outflow speed, and an average passage time of a contrast medium or a blood flow are calculated based on CT images, and indices corresponding to the perfusive-flow index values are displayed in color.

On the other side, the present diagnostic x-ray system receives 3D CT perfusive-flow images from the 3D CT device 23 or PACS device 24 through the network 22, and stores the 3D CT perfusive-flow images into the 3D image memory 16.

During operation, a check on perfusion of the test subject Q and a final check on a medical treatment are made by using X-ray images obtained by the present system 100.

Figure 8:
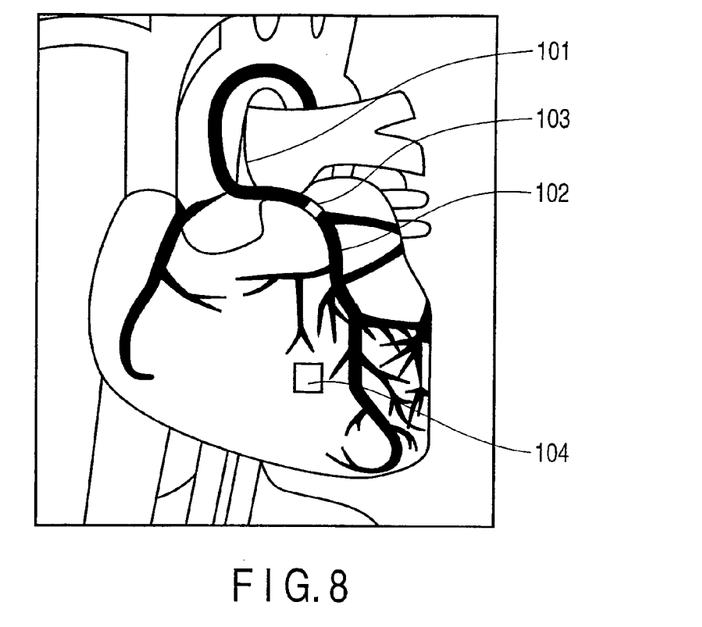
FIG. 8 illustrates ROI set on an image imaging a coronary artery in the diagnostic x-ray system.

In the second flow F2, the present system 100 performs common X-ray angiographic imaging. While or after making a treatment such as a thrombolytic therapy or an intervention for the test subject Q, the present system 100 collects X-ray perfusive-flow images while injecting a contrast medium into the test subject Q. As illustrated in FIG. 8, a catheter 101 is inserted up to a starting portion of a right or left coronary artery 102. A contrast medium is continuously injected from the catheter for a constant time period. The X-ray imaging is performed at least for a period from a time point before starting injection of a contrast medium to elapse of a predetermined time from completion of injection of the contrast medium.

When a contrast medium is injected into the coronary artery 102 through the catheter 101, the present system 100 Collects X-ray perfusive-flow images in synchronization with electrocardiograms. An electrocardiographic cycle for collection is matched with an electrocariographic cycle of images collected by the 3D CT device 23. When there is no motion, e.g., for a head, sequential imaging is performed regardless of electrocardiograms.

X-ray perfusive-flow images by X-ray imaging are collected to calculate perfusion flows of coronary arteries of the test subject Q. When collecting the X-ray perfusive-flow images, the image processing device 10 sets the tube voltage applied to the X-ray bulb tube 2 at the same tube voltage and/or uses the same radiation quality filter as when collecting perfusive-flow images obtained by the 3D CT device 23.

The present system 100 applies the set tube voltage to the X-ray bulb tube 2. The X-ray bulb tube 2 radiates a pulsed X-ray. The X-ray transmits through the test subject Q and enters into the X-ray detector 3. The X-ray detector 3 outputs a signal corresponding to an incident amount of the X-ray. The output signal from the X-ray detector 3 is subjected to digital conversion by the A/D converter 11 and is stored as an X-ray perfusive-flow image into the 2D image memory 12.

After collecting the X-ray perfusive-flow images, images which are substantially not influenced by the contrast medium and respective perfusive-flow images are subjected to a division, among the X-ray perfusive-flow images. Then, natural logarithms are calculated. For a natural logarithm image, a myocardial blood feed area 103 on the coronary artery 102 and plural local myocardial areas 104 on a myocardial area are set. The plural local myocardial areas 104 are set on a myocardial area, and typically include plural pixels. A density corresponding to an amount of the contrast medium at each local myocardial area 104 is typically calculated as an average pixel value. The local myocardial areas 104 each may include only one pixel. The myocardial blood feed area 103 typically has a rectangular shape having a width which is substantially equivalent to or slightly smaller than a blood vessel, and is oriented in an arbitrary direction along the blood vessel. The myocardial blood feed area 103 includes plural pixels. A density equivalent to an amount of the contrast medium in the myocardial blood feed area 103 is typically calculated as an average pixel value. The myocardial blood feed area 103 is set at an arbitrary part of a flow path between an injector and an interested myocardial area, or more specifically, an arbitrary part between an arbitrary part of the catheter or an outlet of the catheter (equivalent to an inlet of a coronary artery) and an interested myocardial area.

Next, in step S1, the perfusive-flow index-value calculation unit 20 calculates perfusive flow indices from an X-ray perfusive-flow image. Calculation of the perfusive-flow indices is carried out in the third flow F3. Perfusive flow indices are described in a known method, for example, according to Jpn. Pat. Appln. KOKAI Publication No. 2008-136800.

The perfusive-flow indices provide three types of perfusive flow indices, i.e., first to third indices $K_1$ to $K_3$. The first index $K_1$ deals with a contrast-medium inflow period until a contrast medium reaches a myocardium. The first index $K_1$ is calculated as a "index $K_1$ expressing an inflow state of blood" concerning a local myocardium, provided that a reference time density curve of a coronary artery is taken as an input function and that a time density curve of a local myocardium at a local myocardial area is taken as an output function.

The second index $K_2$ deals with a contrast-medium outflow period until the contrast medium flows out of the myocardium since the contrast medium reaches the myocardium. The second index $K_2$ is calculated as a "index $K_2$ expressing an outflow state of blood" concerning a local myocardium, provided that a reference time-density curve of a coronary artery is taken as an input function and that a time-density curve at a local myocardial area is taken as an output function.

The third index $K_3$ is calculated from the first index $K_1$ and the second index $K_2$.

The time density curve at a local myocardial area defines a signal component proportional only to an amount of a contrast medium when the contrast medium is applied to a test subject such as a human body is distributed in or passes through coronary arteries and myocardia.

The perfusive-flow index-value calculation unit 20 calculates the first index $K_1$ reflecting an inflow state of blood flowing into an actual local myocardial area, which is proportional to, for example, myocardial blood flow. A target calculation period to calculate the first index $K_1$ is set as a contrast-medium inflow period from a time point when injection from the catheter 101 illustrated in FIG. 8 starts to a time point when injection is complete.

Figure 9:
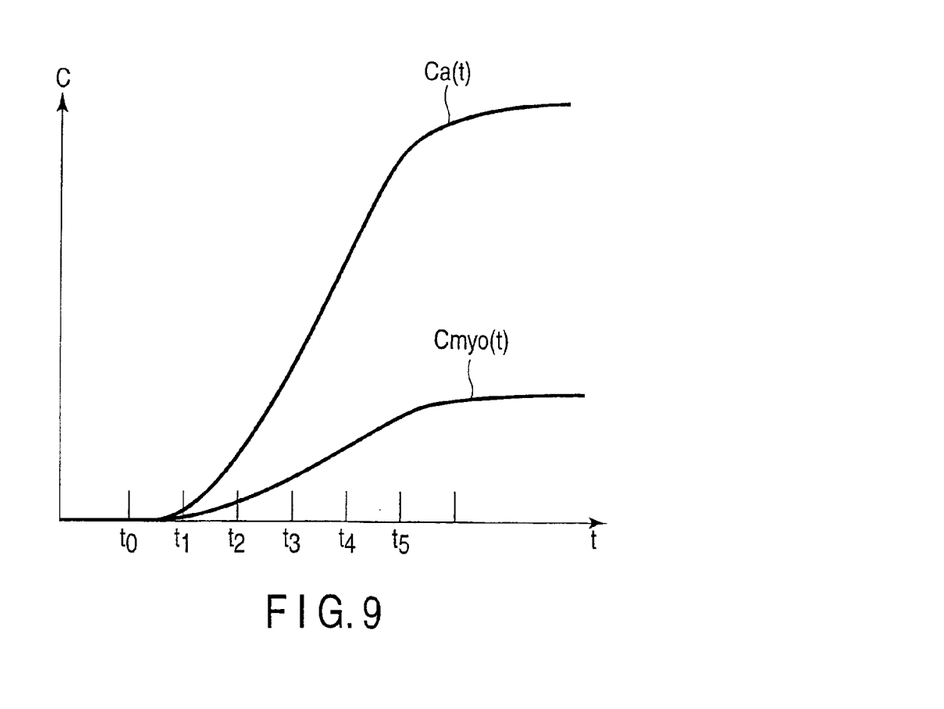
FIG. 9 is a graph representing a time-density curve during an inflow period of a contrast-medium, which is generated by a perfusive-flow index-value calculation unit in the diagnostic x-ray system.

Within the contrast-medium inflow period, plural X-ray perfusive-flow images are collected by the present system 100. From a natural logarithm image calculated by using each of the X-ray perfusive-flow images, a time-density curve Ca(t) and plural time-density curves Cmyu(t) are generated. The time-density curve Ca(t) relates to the blood feed area 103 of a myocardium.

Figure 10:
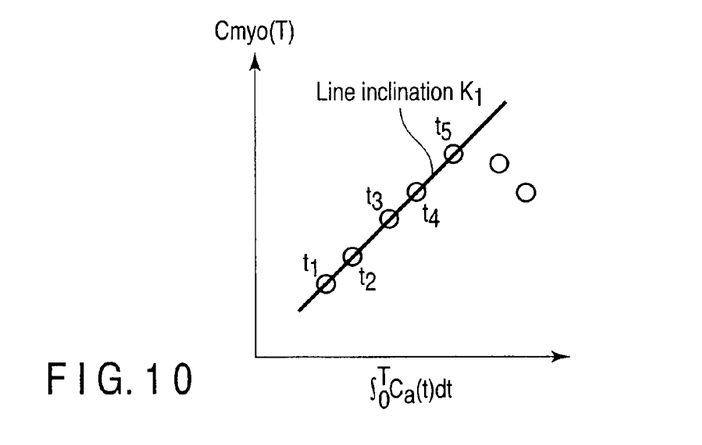
FIG. 10 is a graph representing a first index $K_1$ calculated by the perfusive-flow index-value calculation unit in the diagnostic x-ray system.

Next, the perfusive-flow index-value calculation unit 20 plots a value at each time point, provided that a time integral of a contrast medium (an inflow amount of the contrast medium) ∫Ca(t) is represented by the horizontal axis and that existing amounts of the contrast medium at local myocardial areas 104 are represented on the vertical axis, as represented in FIG. 10. The perfusive-flow index-value calculation unit 20 generates discrete distribution of time-based changes of intake amounts of blood at the local myocardial areas in relation to a blood feed amount to the entire myocardia. The perfusive-flow index-value calculation unit 20 obtains an inclination $K_1$ of a line by performing a linear fitting processing on the discrete distribution of plotted values. The perfusive-flow index-value calculation unit 20 takes the inclination $K_1$ of the line as the first index $K_1$.

The first index $K_1$ quantifies how much a local myocardial area follows a blood feed to the entire myocardia and whether or not blood is received. When the first index $K_1$ is out of a normal range toward a lower value side, the first index $K_1$ implies that inflow of blood at a local myocardial area does not follow inflow of blood into a coronary artery. There is accordingly a possibility that an inflow trouble occurs in the local myocardial area.

The perfusive-flow index-value calculation unit 20 performs the same processing as described above on each of all local myocardial areas 104, to calculate the first index $K_1$, and hence prepares a map of the first index $K_1$.

Next, in step S2, the area extraction unit 17 extracts an interested area from a CT perfusive-flow image. For example, if X-ray perfusive-flow images are collected by imaging only the right coronary artery, the interested area is identified as the blood vessel thereof and a myocardial area of the heart which is nourished by the blood vessel, and the other parts are deleted. Extraction of interested areas is carried out in the fourth flow F4. The area extraction unit 17 receives a 3D CT perfusive-flow image through the network 22 from the 3D CT device 23 or PACS device 24. The area extraction unit 17 manually identifies an area which coincides with an X-ray perfusive-flow image, from the 3D CT perfusive-flow image, and extracts the interested area in the coinciding area from the 3D CT perfusive-flow image. For example, if the X-ray perfusive-flow images are collected by contrast-imaging only the right coronary artery, the extracted perfusive-flow image expresses perfusion flows of myocardia due to influence on the right coronary artery. Without this extraction processing, the 3D CT perfusive-flow image include influences not only from the right coronary artery but also the left coronary artery, atria and ventricles of the heart, and main arteries. This is because 3D CT perfusive-flow images are usually imaged from a state in which blood containing a contrast medium is fed out into the heart and all blood vessels by injecting the contrast medium through a vein. The perfusive-flow image extracted from the interested area in the 3D CT perfusive-flow image (hereinafter referred to as a 3D CT perfusive-flow image) is sent to the CT image projection unit 18.

In step S3, the CT-image projection unit 18 receives information concerning a projection direction of the X-ray perfusive-flow image obtained by the present system 100, from inspection information stored in the 2D image memory 12. The CT-image projection unit 18 projects the perfusive-flow image of the interested area extracted by the area extraction unit 17, in the same direction as a projection direction in which the X-ray perfusive-flow image is obtained by the diagnostic x-ray system, as illustrated in FIG. 3A and FIG. 3B. The CT-image projection unit 18 projects the perfusive-flow image of the interested area for each cardiac phase. The CT image projection unit 18 performs projection for each of the 3D CT perfusive-flow images. The projection is performed along the fifth flow. Specifically, the CT image projection unit 18 projects the perfusive-flow image of the interested area extracted by the area extraction unit 17, in the same projection direction as X-ray perfusive-flow images are obtained, under the same conditions as those for the X-ray geometry. A projection image of a perfusive-flow image which reflects perfusive flows only in the interested area is obtained by the projection.

Next, in step S4, the positioning unit 19 performs positioning of an X-ray perfusive-flow image obtained by the present Diagnostic x-ray system and a CT perfusive-flow image from the 3D CT device 23. Positioning is performed in the sixth flow.

Based on an image including, for example, artery information in the perfusive-flow projection image of the interested area obtained through projection by the CT-image projection unit 18, the positioning unit 19 performs positioning between an X-ray perfusive-flow image and a CT perfusive-flow image which include the same artery information as each other. The positioning unit 19 performs positioning, based on a shape of a coronary artery in the heart of the test subject Q or an outer shape of the heart, for example, as the test subject Q.

Next, in step S5, the perfusive-flow index-value calculation unit 20 calculates perfusive flow indices $K_1$, $K_2$, and $K_3$ representing a thrombolytic therapy and a perfusive-flow state before an intervention treatment, from the perfusive-flow projection image of the interested area extracted from the 3D CT device 23 (hereinafter referred to as an interested projection image based on 3D CT), in the same manner as the perfusive-flow indices $K_1$, $K_2$, and $K_3$ are calculated from X-ray perfusive-flow images. Details of the perfusive flow indices $K_1$, $K_2$, and $K_3$ are described in the known method described above, e.g., Jpn. Pat. Appln. KOKAI Publication No. 2008-136800. The perfusive-flow index-value calculation unit 20 calculates the first index $K_1$ representing an inflow state of blood, the second index $K_2$ representing an outflow state of blood, and the third index $K_3$ calculated from the first index $K_1$ and second index $K_2$.

Next, in the density correction unit 27, the second area-specifying unit 27-1 specifies areas where perfusive flows do not change before and after a medical treatment in the 3D CT perfusive-flow image and the X-ray perfusive-flow image obtained by the present system 100. The correction unit 27-2 performs a correction, in flow F7, in a manner that perfusive-flow indices $K_1$, $K_2$, and $K_3$ in each of the areas specified by the second area-specifying unit 27-1 and perfusive-flow indices $K_1$, $K_2$, and $K_3$ calculated from the interested projection image based on 3D CT respectively coincide with each other, respectively.

As a result of the correction, the X-ray perfusive-flow indices $K_1$, $K_2$, and $K_3$ and the perfusive-flow indices $K_1$, $K_2$, and $K_3$ calculated from the interested projection image based on 3D CT respectively coincide with each other. An X-ray perfusive-flow index image and a perfusive-flow index image calculated from the interested projection image based on 3D CT are displayed, for example, arranged regularly on the screen of the display device 26. For example, a perfusive-flow index $K_1$ for an unchanged area in an X-ray perfusive-flow image is supposed to be "1". A perfusive-flow index $K_1$ for a corresponding portion in a perfusive-flow image calculated from an interested projection image based on 3D CT is supposed to be "10". Then, the perfusive-flow index "1" in an X-ray perfusive-flow index image is corrected to "10". Perfusive-flow indices $K_1$ for other portions in the X-ray perfusive-flow index image are also corrected in a similar manner. The perfusive-flow index "10" for the unchanged part in the X-ray perfusive-flow index image coincides with the perfusive-flow index "10" for the corresponding portion in the perfusive-flow index image calculated from the interested projection image based on 3D CT. On the one single screen of the display device 26, the other portions therefore become comparable from a viewpoint of comparison with a ratio to a coincident unchanged part perfusion index. The unchanged part means an area where perfusive flows do not change due to influence of a medical care.

Next, in step S6, the comparative-index calculation unit 21 calculates comparative indices between the X-ray perfusive flow indices $K_1$, $K_2$, and $K_3$ corrected by the density correction unit 27 and the perfusive flow indices $K_1$, $K_2$, and $K_3$ calculated from the interested projection image based on 3D CT. Calculation of the comparative indices is performed in flow F8. The comparative-index calculation unit 21 compares the perfusive flow indices $K_1$, $K_2$, and $K_3$, which are calculated from X-ray perfusive-flow images on the basis of positioning information by the positioning unit 19, with the perfusive flow indices $K_1$, $K_2$, and $K_3$ calculated from the interested projection image based on 3D CT, respectively. As a result of comparison, the comparative-index calculation unit 21 calculates comparative indices C between the X-ray perfusive flow indices $K_1$, $K_2$, and $K_3$ and the perfusive flow indices $K_1$, $K_2$, and $K_3$ calculated from the interested projection image based on 3D CT, respectively. The comparative indices C are ratios or differences between the X-ray perfusive flow indices $K_1$, $K_2$, and $K_3$ and the perfusive flow indices $K_1$, $K_2$, and $K_3$ calculated from the interested projection image based on 3D CT, respectively.

Figure 11:
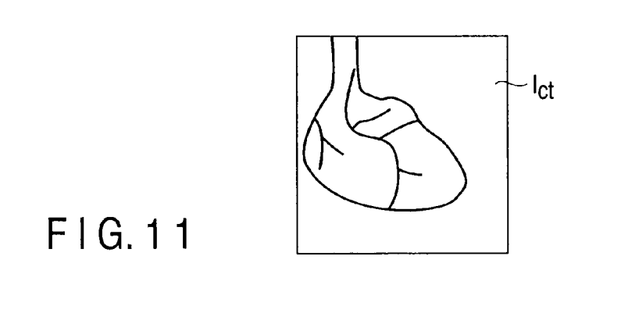
FIG. 11 illustrates an example of a CT image Ict obtained by the 3D CT device before a medical operation.
Figure 12:
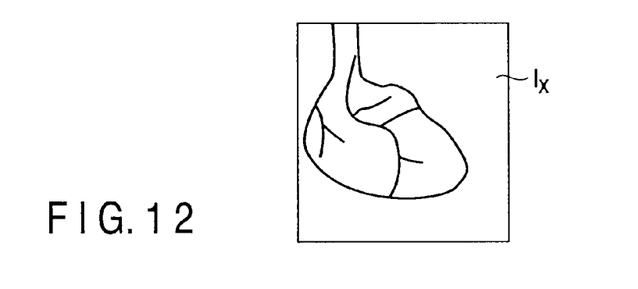
FIG. 12 illustrates an example of an X-ray image Ix obtained by the 3D CT device during a medical operation by the diagnostic x-ray system.

For example, FIG. 11 illustrates a CT image Ict obtained by the 3D CT device 23 before a medical operation. The CT image Ict represents an example of coronary arteries of the test subject Q. FIG. 12 illustrates an example of an X-ray perfusive-flow image Ix obtained by the present system 100 during a medical operation. The X-ray perfusive-flow image Ix also represents an example of coronary arteries of the test subject Q.

The CT image Ict and the X-ray perfusive-flow image Ix are subjected to positioning.

The first to third perfusive-flow indices $K_1$, $K_2$, and $K_3$ of the CT image Ict are calculated.

The first to third perfusive-flow indices $K_1$, $K_2$, and $K_3$ of the X-ray image Ix are calculated.

A correction is made in a manner that the first to third perfusive-flow indices $K_1$, $K_2$, and $K_3$ for an unchanged portion of the X-ray image Ix and the first to third perfusive-flow indices $K_1$, $K_2$, and $K_3$ for the corresponding portion in the CT image Ict coincide with each other.

The comparative indices C are obtained as ratios or differences between the X-ray perfusive flow indices $K_1$, $K_2$, and $K_3$ and the perfusive flow indices $K_1$, $K_2$, and $K_3$ calculated by using CT perfusive-flow images.

Figure 13:
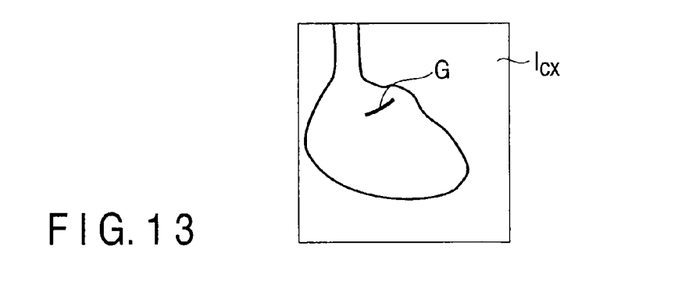
FIG. 13 illustrates an image Icx where an comparative index C is overlapped on the X-ray image Ix by the diagnostic x-ray system.

FIG. 13 illustrates an image Icx in which the comparative indices C are overlapped on the X-ray image Ix. On the display screen of the display device 26, for example, an image of the comparative indices C and the X-ray image Ix may be displayed and arranged regularly. For example, in what area of myocardia a medical care caused blood flow to recover after the care can be visualized. This figure illustrates a recovery portion G where blood flow has recovered. Quantitativity is given because of not depending on a visual check. Since comparison is available between before and after a medical treatment (medical care), how much a blood flow volume has increased can be understood, i.e., how much blood feed to a myocardium has improved can be understood.

The comparative indices C calculated by the comparative-index calculation unit 21 are displayed on the display device 26, arranged regularly together with perfusive flow indices of the X-ray perfusive-flow image. The X-ray perfusive-flow indices $K_1$, $K_2$, and $K_3$ and the comparative indices C may be displayed, for example, switched by a switch.

Thus, according to the embodiment described above, an interested image extracted from a 3D CT perfusive-flow image is projected in the same direction as a projection direction of obtaining X-ray perfusive-flow images. X-ray perfusive-flow images and CT perfusive-flow images are subjected to positioning. Perfusive flow indices K, such as perfusive flow indices $K_1$, $K_2$, and $K_3$, are calculated from the X-ray perfusive-flow images and from the CT perfusive-flow images. Based on positioning information, an X-ray perfusive index image and a CT perfusive index image are subjected to positioning. A correction is performed in a manner that the perfusive flow indices $K_1$, $K_2$, and $K_3$ in an unchanged part in the X-ray perfusive-flow index image and those in the CT perfusive-flow index image coincide with each other. Then, comparative indices C between the X-ray perfusive-flow index image and the CT perfusive-flow index image are calculated.

In practicing perfusion using CT images and X-ray images of a coronary artery of a test subject, inflow and outflow states of blood in a coronary artery of a test subject can be checked. These states are checked before and after a medical care such as a thrombolytic therapy or an intervention. In general, perfusion is performed with use of CT images before a medical care. In a final stage of a medical care, perfusion is performed with use of X-ray images. To identify therapy effects, perfusion need be compared between before and after a medical care. Perfusion cannot be directly compared between different modalities or different contrast-imaging methods. According to the present system, an area occupied by a blood vessel, which is imaged by X-rays, is extracted as an interested area from a CT image, and perfusion obtained from an X-ray image and perfusion obtained from a CT image are corrected so as to coincide with each other in an unchanged part. In this manner, even if different modalities and different contrast-imaging methods are employed, the present system is capable of comparing perfusion obtained by different modalities and by different contrast-imaging methods.

In practicing perfusion using CT images and X-ray images of a coronary artery of a test subject, improvements in inflow and outflow states of blood between before and after a medical care are grasped by knowing improvements in inflow and outflow states of blood into and from the coronary artery of the test subject, i.e., by checking indices. Since CT perfusion and X-ray perfusion are configured to be comparable with each other, perfusion can be compared between before and after a medical care without increasing an exposure dose of X-rays exposed to a test subject Q to obtain X-ray perfusion images before the medical care.

A difference between CT and X-ray angiographic imaging (an angiographic examination method) exists in whether a method for injecting a contrast medium is a intra-arterial injection type or a transvenous injection type. Conditions for perfusion vary depending on whether intra-arterial injection or transvenous injection is used. The conditions are the density of a contrast medium and whether pressure when injecting the contrast medium directly influences or not. The present system 100 is effective if the method for injecting a contrast medium is intra-arterial injection, if an injection speed of injection of the contrast medium is controlled, and if exacerbation of injection pressure of the contrast medium can be restricted within a constant range.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A diagnostic X-ray system, the system comprising:
an image processing device including a CT-image projection unit that obtains a third perfusive-flow image of a coronary artery by projecting a second perfusive-flow image of the coronary artery obtained by a computed tomography (CT) apparatus in a projection direction, the projection direction being a same direction as a direction in which an X-ray is projected toward a test subject to obtain a first perfusive-flow image of the coronary artery;
a memory configured to store the first perfusive-flow image;
the image processing device including a positioning unit that obtains positioning information by performing position alignment of the first perfusive-flow image and the third perfusive-flow image based on the shape of the coronary artery or an outer shape of the heart;
the image processing device including a perfusive-flow index calculation unit that calculates a first perfusive-flow index from the first perfusive-flow image, and calculates a second perfusive-flow index from the third perfusive-flow image;
the image processing device including a comparative-index calculation unit that calculates a comparative-index based on the first perfusive-flow index and the second perfusive-flow index, the comparative-index calculated from a ratio or difference between the first perfusive-flow index and the second perfusive-flow index, based on the positioning information obtained by the positioning unit,
wherein the first perfusive-flow image is obtained during or after a medical treatment on the test subject,
the second perfusive-flow image is obtained by the computed tomography apparatus before the medical treatment on the text subject, and
the positioning unit performs positioning of the first perfusive-flow image obtained during or after the medical treatment and the third perfusive-flow image obtained before the medical treatment; and
a display device that displays the comparative-index calculated by the comparative-index calculation unit,
wherein the comparative-index and the first perfusive-flow index arranged together or are synthesized with each other.

2. The diagnostic X-ray system according to claim 1, wherein the second perfusive-flow image includes a CT image for calculating perfusive-flow 3. The diagnostic X-ray system according to claim 1, wherein the computed tomography apparatus comprises an X-ray bulb tube that is applied with a tube voltage to radiate an X-ray, and a radiation quality filter provided on a radiation path of the X-ray radiated from the X-ray bulb tube, and the first perfusive-flow image is collected by one or both of the same tube voltage and the same radiation quality filter as when collecting the second perfusive-flow image.

4. The diagnostic X-ray system according to claim 1, wherein the CT-image projection unit of the image processing device comprises:
an area specifying unit that specifies an image area on the second perfusive-flow image; and
a projection unit that projects only the image area specified by an area extraction unit.

5. The diagnostic X-ray system according to claim 1, wherein the density correction unit of the image processing device comprises:
an area specifying unit that specifies areas respectively in an image of the first perfusive-flow index and an image of the second perfusive-flow index, the areas mutually corresponding to each other, and
a correction unit that corrects the first and second perfusive-flow indices in a manner that the first and second perfusive-flow indices coincide with each other between the areas specified by the area specifying unit.

6. The diagnostic X-ray system according to claim 1, wherein the perfusive-flow index correction unit calculates, from the first perfusive-flow image, a first index for an inflow period of a contrast medium until the contrast medium reaches a target portion of the test subject, and/or a second index for an outflow period of the contrast medium until the contrast medium flows out of the target portion since the contrast medium reaches the target portion.

7. The diagnostic X-ray system according to claim 1, wherein the perfusive-flow index correction unit calculates, from the third perfusive-flow image, a first index for an inflow period of a contrast medium until the contrast medium reaches a target portion of the test subject, and/or a second index for an outflow period of the contrast medium until the contrast medium flows out of the target portion since the contrast medium reaches the target portion.

8. The diagnostic X-ray system according to claim 1, wherein the comparative-index calculation unit further causes the display to display a comparative-index calculated from a ratio or difference between a first index calculated from the first perfusive-flow image and a first index calculated from the second perfusive-flow image, and/or a comparative-index calculated from a ratio or difference between a second index calculated from the first perfusive-flow image and a second index calculated from the second perfusive-flow image.

9. A diagnostic X-ray method, the method comprising the following steps:
obtaining, by a CT-image projection unit of an image processing device, a third perfusive-flow image of a coronary artery by projecting a second perfusive-flow image of a coronary artery obtained by computed tomography in a projection direction, the projection direction being a same direction as a direction in which an X-ray is projected toward a test subject to obtain a first perfusive-flow image of a coronary artery;
storing, by a memory, the first perfusive-flow image;
obtaining, by a positioning unit of the image processing device, positioning information by performing position alignment of the first perfusive-flow image and the third perfusive-flow image based on the shape of the coronary artery or an outer shape of the heart;
calculating, by a perfusive-flow index calculation unit of the image processing device, a first perfusive-flow index from the first perfusive-flow image, and calculating a second perfusive-flow index from the third perfusive-flow image;
calculating, by a comparative-index calculation unit of the image processing device, a comparative-index based on the first perfusive-flow index and the second perfusive-flow index, the comparative-index calculated from a ratio or difference between the first perfusive-flow index and the second perfusive-flow index, based on the positioning information,
wherein the first perfusive-flow image is obtained during or after a medical treatment on the test subject,
the second perfusive-flow image is obtained by the computed tomography before the medical treatment on the text subject, and
the step of obtaining positioning information includes performing positioning of the first perfusive-flow image obtained during or after the medical treatment and the third perfusive-flow image obtained before the medical treatment; and
displaying, by a display device, the comparative-index calculated by the comparative-index calculation unit,
wherein the comparative-index and the first perfusive-flow index are arranged together or are synthesized with each other.

* * * * *